United States Patent [19]

Suzuki et al.

[11] 4,222,843
[45] Sep. 16, 1980

[54] COLORING-DECOLORING APPARATUS FOR ELECTROPHORETIC SYSTEMS

[75] Inventors: Hideo Suzuki, Tokyo; Toshihide Fujiwara, Fuchu; Nobutaka Kaneko, Hachiouji, all of Japan

[73] Assignee: Olympus Optical Co., Ltd., Tokyo, Japan

[21] Appl. No.: 33,170

[22] Filed: Apr. 25, 1979

[30] Foreign Application Priority Data

Apr. 27, 1978 [JP] Japan .............................. 53-55254[U]
Apr. 27, 1978 [JP] Japan .............................. 53-55255[U]

[51] Int. Cl.² ............................................ C25D 1/12
[52] U.S. Cl. ............................ 204/299 R; 204/180 G; 204/300 R
[58] Field of Search ........... 204/180 G, 180 S, 180 R, 204/299 R, 300 R; 424/12; 23/230 B; 118/9, DIG. 15, 409, 416

[56] References Cited

U.S. PATENT DOCUMENTS

| | | | |
|---|---|---|---|
| 1,174,946 | 3/1916 | Illig | 204/300 R |
| 3,753,885 | 8/1973 | Hammond, Jr. | 204/300 R X |
| 3,813,327 | 5/1974 | Crowne et al. | 204/300 R |
| 3,898,151 | 8/1975 | Nessar | 204/300 R |
| 3,930,880 | 1/1976 | Hoefer | 204/299 R X |
| 4,115,234 | 9/1978 | Anselrode | 204/180 R |

*Primary Examiner*—Arthur C. Prescott
*Attorney, Agent, or Firm*—Cushman, Darby & Cushman

[57] ABSTRACT

A coloring-decoloring apparatus for electrophoretic system comprising a bonding drum, a support plate, two rollers arranged in contact with the outer circumference of said bonding drum and a liquid trough. Said coloring-decoloring apparatus functions to color and decolor a sample carrier with coloring or decoloring liquid agent while holding said sample carrier onto said bonding drum with said two rollers and rotating said drum, and has a circumferential section which is lower in curvature than the imaginary circular circumference of said bonding drum and serves to prevent said sample carrier from being deformed or torn due to contraction even when said sample carrier is dried while being held onto said bonding drum.

4 Claims, 7 Drawing Figures

COLORING-DECOLORING APPARATUS FOR ELECTROPHORETIC SYSTEMS

BACKGROUND OF THE INVENTION a. Field of the Invention

The present invention relates to an apparatus for coloring and decoloring sample carriers in electrophoretic systems.

b. Description of the Prior Art

The electrophoresis technique is used for measuring proteins contained in blood serum for clinical inspections in medical institutes. This analysis is carried out, as already known to those skilled in the art, by applying blood serum to be analysed onto a sample carrier made, for example, of cellulose acetate paper or the similar material and electrically energizing the sample carrier to develop fractionated patterns of the blood serum, whereafter the electrically energized sample carrier is colored with a coloring liquid agent and, after the areas other than the blood serum are decolored, the sample is measured with a colorimeter for quantitative determination. Conventionally, various processes of this analysis were manually carried out with low efficiency. Further, analysis by electrophoresis required highly delicate skill and the conventional electrophoretic system had a defect that analytical results were different depending on individual analysts' measuring skills. In view of such circumstances, it has been attempted to develop automatic electrophoretic systems which can automatically carry out the processes of electrophoresis for the purpose of enhancing measuring efficiency and eliminating analytical variations due to difference in measuring skills depending on individual analysts. In order to carry out the coloring and decoloring steps out of the various area in the automatic electrophoretic systems thus developed, such an apparatus as is illustrated in FIG. 1 and FIG. 2 has been designed for coloring, decoloring and drying sample carriers. This conventional coloring-decoloring-drying apparatus will be described below:

In FIG. 1 and FIG. 2, the reference numeral 1 represents a casing which is mounted on a stand designated by the reference numeral 2. The reference numerals 3 and 4 denote rollers respectively which are attached to mounting brackets 5 and 6 in the vicinity of entrance 1a of the casing 1. The reference numerals 7 and 8 represent a light emitting diode and an optical detector element respectively which are arranged over and under the entrance 1a so as to provide a system for detecting a sample carrier. The reference numeral 9 denotes a bonding drum which is rotatably arranged in the casing 1 in a manner described later and has a central concave section 9a which is lower than both side edges 9b along the circumferential surface as shown in FIG. 2. Fixed to both the side edges 9b and portion of the concave section 9a of the bonding drum 9 are members 9d and 9e which are made of sponge or the similar material and are to be used for bonding a sample carrier. The reference numerals 10 and 11 represent rollers which are attached to a support plate 12 respectively. Of these rollers, the roller 10 is always kept in contact with the bonding drum by an adequate means such as a spring which pulls said roller toward the center of the bonding drum. The reference numeral 13 represents a sample carrier guide which is attached to the support plate 12. The reference numerals 14, 15 and 16 designate rollers respectively and the reference numeral 17 denotes a carrier support guide. These rollers and carrier guide are quite the same as those described above. Now the mechanism for rotating the bonding drum will be described with reference to FIG. 2.

The reference numeral 20 represents a first motor, the reference numerals 21 and 22 designate gears respectively and the reference numeral 23 denotes a one-way clutch which functions to transmit rotation of the gear 22 to the shaft 9c of the drum only when the gear rotates, for example, clockwise as seen from the right side of the figure. The reference numeral 25 represents a second motor. The reference numerals 26 and 27 designate gears respectively and the reference numeral 28 denotes a shaft to which the gear 27 is fixed and whose one end is fixed to the support plate 12. The reference numeral 29 represents a one-way clutch which transmits rotation of the gear to the shaft 9c of the bonding drum only when the gear rotates counterclockwise as seen from the left side of the figure. The reference numeral 30 represents a trough containing, for example, a coloring liquid agent and is movable up and down by an adequate hoist means through an opening 2a formed in the stand 2 in such a manner that the trough is hoisted up from the position shown in the figure into the casing 1 through the opening 2a until the lower portion of the bonding drum 9 is dipped into the coloring liquid agent 31. Further, the reference numeral 32 used in FIG. 2 represents a duct which has the other end (not shown) connected to a drying air blower and through which dry air is to be blown for drying the sample carrier.

Now, operations of the conventional coloring-decoloring-drying apparatus will be described below. First, a sample carrier with fractionated patterns formed by applying blood serum onto the sample carrier made of cellulose acetate paper or the similar material and electrically energizing it is inserted through the entrance 1a. In the coloring-decoloring-drying apparatus, the insertion of the sample carrier is detected with a carrier detecting system consisting of the light emitting diode 7 and optical detector element 8, and the bonding drum 9 is rotated. Speaking more detailedly, the first motor 20 shown in FIG. 2 starts to rotate the bonding drum 9. In this case, the first motor 20 is rotated in such a direction as to turn the gear 22 clockwise as seen from the right side of FIG. 2 so that rotation of the gear 22 is transmitted to the shaft 9c which in turn rotates the bonding drum 9. By this rotation, the sample carrier is fed to the surface of the bonding drum 9 and adheres onto the circumference thereof, whereafter said sample carrier is finally held in a condition bonded to the member 9d made of sponge or the similar material of the bonding drum 9. In this step, the starting position of the bonding drum 9 is set in such a manner that the member 9e fixed to said drum will just meet the leading end of the sample carrier when it just reaches the surface of the bonding drum 9. Therefore, the leading end of the sample carrier first adheres to the member 9e and the sample carrier is fed while gradually adhering to the member 9d which is fixed on both the sides of the bonding drum 9. Further, the length of the surface of the bonding drum 9 as measured from the roller 10 to the roller 14 is selected so as to be a little shorter than the length of the sample carrier and the rotation of the bonding drum 9 is stopped after the sample carrier adheres onto the bonding drum 9, and the leading end of the sample carrier is inserted between the bonding drum 9 and the roller 14. Hence, both the ends of the sample carrier are caught between the bonding drum 9 and rollers 10 and 14 respectively, whereby the sample carrier is held in a condition adhering to the bonding drum 9. In this condition, the second motor 25 starts rotating. In this step, the second motor 25 is rotated in such a direction as to turn the gear counterclockwise as seen from the left side of FIG. 2. Hence, the shaft 28 which is fixed to the gear 27 rotates also in the same direction and the shaft 9c of the bonding drum 9 is rotated through the one-way clutch 29. Accordingly, the support plate 12 which is fixed to the shaft 28 is turned together with the bonding drum 9. Therefore, the sample carrier is rotated as a whole with both its ends held between the bonding drum 9 and the rollers 10 and 14 respectively. When the bonding drum 9 makes half a turn to place the sample carrier at its lowermost position, the motor 25 stops operating. In this condition, the bonding drum 9, support plate 12, roller 10, etc. are kept stationary at the positions just vertically inverted from those shown in the figure. With the members kept in these positions respectively, the coloring liquid trough 30 is hoisted up until the lower portion of the bonding drum 30 is dipped into the coloring liquid agent 31. Therefore, the sample carrier fixed to the bonding drum 9 is also dipped into the coloring liquid agent. The sample carrier is maintained in this position for a definite time to be colored with the liquid agent. After the sample carrier has been colored, the coloring liquid trough 30 is hoisted down and a decoloring liquid trough (not shown) having the same construction as that of the coloring liquid trough is inserted instead through the opening 2a of the stand 2, whereby the colored sample carrier is dipped into a decoloring liquid agent and decolored in the area other than the blood serum. After the sample carrier has been decolored in this way, the decoloring liquid trough is shifted out of the casing 1 and warm air is blown into the casing 1 to dry the sample carrier. After the sample carrier has been colored, decolored and dried, the motor 25 is rotated again to turn the bonding drum 9, support plate 12, rollers 10 and 14, etc. as a whole in the manner already described above. When these members are returned to their initial positions respectively, the second motor 25 is stopped and the first motor 20 is rotated to turn the bonding drum 9 together with the sample carrier. In this case, however, the tip of the guide plate 17 which is a little protruding inside the bonding drum 9 serves to peel off the sample carrier from the surface of the bonding drum, whereby the sample carrier passes between the roller 14 and guide plate 17, and is sent to the next stage through the exit 1b of the casing 1. On the conventional coloring-decoloring-drying device described above, the sample carrier is elongated while it is soaked with the coloring liquid agent or decoloring liquid agent, but contracts after are dried. Since both the ends of the sample carrier is fixed between the drum and the rollers respectively, the sample carrier is often deformed or torn after it is dried. The conventional coloring-decoloring-drying apparatus had such a defect.

Further, the conventional apparatus had another defect that it is designed unavoidably as a large unit since it functions to bond the sample carrier onto the bonding drum 9 accommodated in the casing 1 and to dip the sample carrier into liquid agent by hoisting up the coloring or decoloring liquid trough into the casing 1 from outside said casing.

SUMMARY OF THE INVENTION

A primary object of the present invention is to provide a coloring-decoloring apparatus for use with electrophoretic systems which can correct the defect of the conventional coloring-decoloring-drying apparatus and has a superficial section on the circumference of a bonding drum which is lower in curvature than the imaginary circular circumference of said drum and functions to hold a sample carrier in a loose condition while it is soaked but in a less loose condition after it is dried along the circumference of said bonding drum. Another object of the present invention is to provide a compact coloring-decoloring apparatus for use with electrophoretic systems which utilizes the casing itself as the liquid trough and therefore requires no coloring liquid trough, decoloring liquid trough, spaces for arranging such troughs or hoist mechanism therefor.

DETAILED DESCRIPTION OF THE PREFERRED EMBODIMENT

Figure 3:
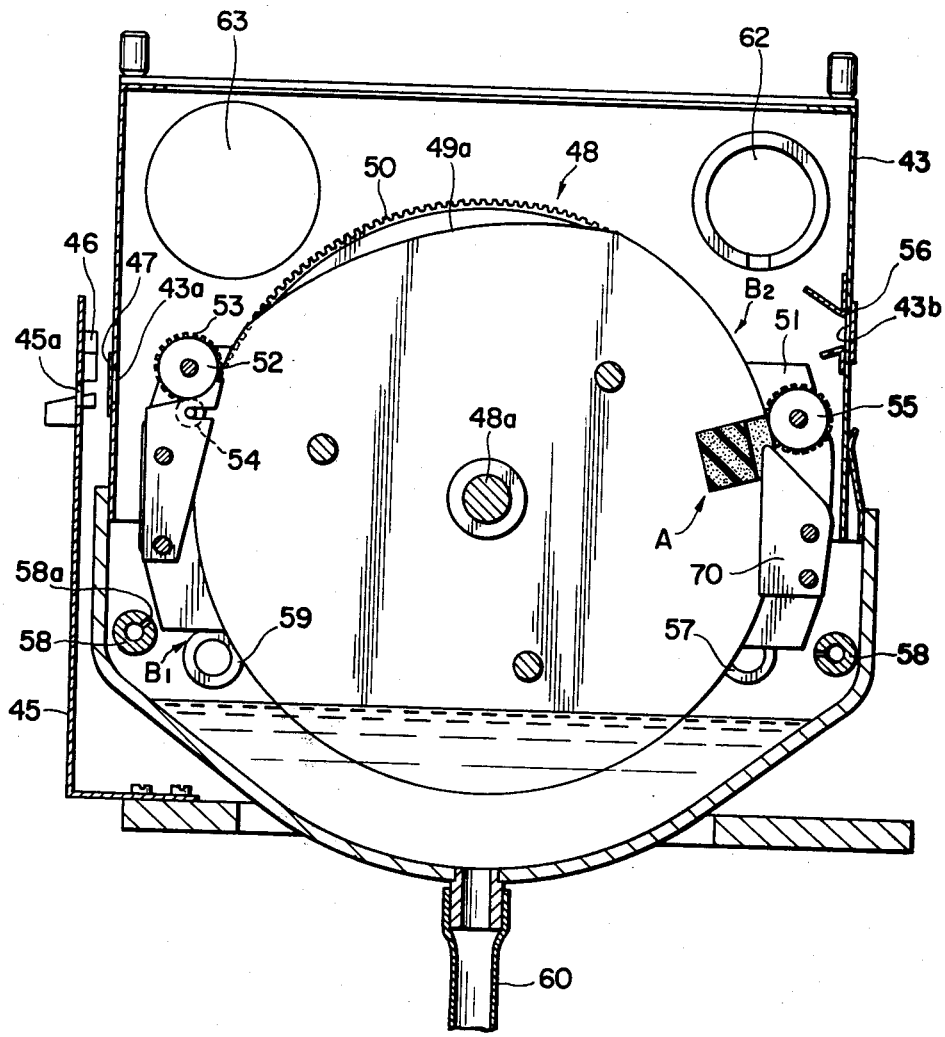
FIG. 3 and FIG. 4 show sectional side elevational views illustrating the construction of the coloring-decoloring apparatus for use with an electrophoretic system according to the present invention.
Figure 4:
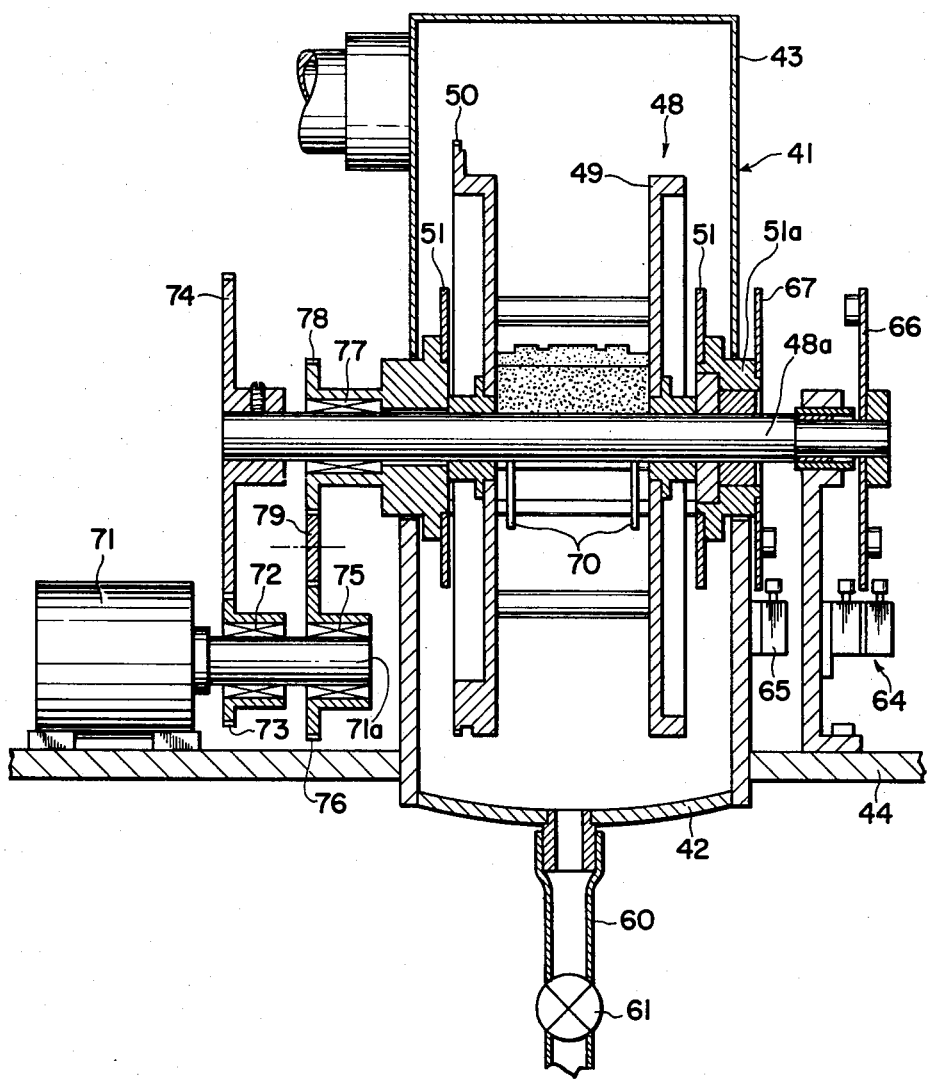

Referring now to an embodiment shown in the accompanying drawings, the coloring-decoloring apparatus according to the present invention will be described more detailedly below. In FIG. 3 and FIG. 4, the reference numeral 41 represents a casing which consists of a liquid trough 42 and a cover 43. The reference numeral 44 designates a base stand for fixing the casing 41 and the reference numeral 45 denotes a holder plate having an opening 45a through which a sample carrier is to be passed. The reference numeral 46 represents a photo sensor which is arranged in the vicinity of the opening 45a of the holder plate 45. The reference numeral 47 designates a shutter for opening and closing the entrance opening 43a formed in the cover 43 of the casing 41 and the reference numeral 48 denotes a bonding drum having a sample carrier bonding member 49 and a gear 50 which is attached to one side thereof or formed integrally therewith. Of these component parts, the sample carrier bonding member 49 has a surface 49a having a curvature lower than that of the imaginary circular circumference of the bonding drum 48. The reference numeral 51 represents a support plate and the reference numeral 52 designates a first roller which is attached to the support plate 51 and is equipped on one side thereof with a gear 53 in engagement with the gear 50 attached to the bonding drum 48 for forcibly rotating said roller 52 with rotation of the bonding drum 48.

The reference numeral 54 denotes a second roller which is attached to the support plate 51 and is so arranged as to be in contact with the roller 52. The reference numeral 55 represents a third roller attached to the support plate 51. The reference numeral 56 designates a shutter for opening and closing an exit opening 43b formed in the cover 43 of the casing 41, the reference numeral 57 denotes a pipe which is to be used for injecting coloring liquid agent and has a tip located inside the liquid trough 42 of the casing 41. The reference numeral 58 represents a pipe which is to be used for injecting decoloring liquid agent and has a tip located also inside the liquid trough 42 and equipped with a liquid splashing port 58a. The reference numeral 59 designates a pipe for overflowing excess liquid agent. The reference numeral 60 denotes a drain pipe connected to a draining port formed on the bottom of the liquid trough 42. The reference numeral 61 represents a valve arranged in the course of the drain pipe 60. The reference numeral 62 designates a duct for blowing warm air for drying the sample carrier, and the reference numeral 63 denotes a duct for exhausting air out of the casing 41. Further, the reference numerals 64 and 65 represent microswitches respectively. The reference numeral 66 designates a pin holder plate for supporting a pin which is arranged for actuating the microswitch attached to the shaft 48a of the bonding drum 48 and the reference numeral 67 denotes a pin holder plate attached to the shaft 51a of the support plate 51. These microswitches 64 and 65 as well as pins attached to the pin holder plates are provided in plural numbers respectively although each of them is shown in a singular number at an approximate position thereof for clarity of the drawings. However, numbers and locations of these members are appropriately selectable as is apparent to those skilled in the art from the functions thereof which will be described later.

The reference numeral 71 represents a driving motor, and the reference numeral 72 designates a one-way clutch which is mounted on shaft 71a of the motor 71 and functions to transmit rotation of the shaft to gear 73 only when the shaft 71a is turned counterclockwise as seen from the right side of the drawing. The reference numeral 74 denotes a gear which is fixed to the shaft 48a of the bonding drum 48 and in mesh with the gear 73, and the reference numeral 75 represents another one-way clutch which is mounted on the motor shaft 71a and functions to transmit rotation of the shaft to gear 76 only when said shaft is turned clockwise as seen from the right side of the drawing. The reference numeral 77 designates a third one-way clutch which is mounted on the shaft 48a and functions to transmit rotation of the gear 78 to the shaft 48a only when said gear is turned clockwise as seen from the right side of the drawing. The gear 78 is fixed to the support plate 51 and in mesh with the gear 76 by way of gear 79.

When the shaft 71a is turned counterclockwise as seen from the right side of the drawing by driving the motor 71 in a driving system having such a construction as is described above, the rotation of the shaft 71a is transmitted to the gear 73 by way of the one-way clutch 72. The rotation of the gear 73 is transmitted to the gear 74, which in turn rotates the shaft 48a and the bonding drum 50 accordingly. Since the rotation of the shaft 71a is not transmitted to the gear 76 and the rotation of the shaft 48a is not transmitted to the gear 78 during the operations described above, the support plate 51 is not rotated either. Describing in short, the bonding drum 50 alone is rotated when the shaft 71a is turned counterclockwise. During this operation, the support plate is freely rotatable and may therefore turn arbitrarily. Arbitrary rotation of the support plate will be inconvenient, for example, for the stage where a sample carrier is bonded to the bonding drum as is described later. In order to prevent such inconvenience, the gear 70 may be equipped with a fixing means such as an electromagnetic brake which serves to fix the support plate while it is not necessary to turn said support plate. When the shaft 71a is turned clockwise as seen from the right side of the drawing, in contrast, the gear 76 is rotated through the one-way clutch 75. The rotation of the gear 76 is transmitted to the gear 78 by way of the gear 79. The rotation of the gear 78 causes rotation of the support plate 51. Since the gear 78 rotates clockwise at this time as seen from the right side of the drawing, its rotation is transmitted to the shaft 48a through the one-way clutch 77. Therefore, the shaft 48a is rotated together with the gear 78, thereby turning the support plate with the bonding drum as an assembly. When the shaft 71a is driven by the motor 71 so as to turn clockwise as seen from the right side of the drawing as described above, no rotation is transmitted to the gear 73 by way of the clutch 72. In contrast, the shaft 48a is so rotated as to cause rotations of the gear 73 and 74 accordingly. However, since the shaft 48a rotates clockwise as seen from the right side of the drawing, the gear 73 is turned counterclockwise and does not interfere with rotation of the shaft 71a.

Figure 1:
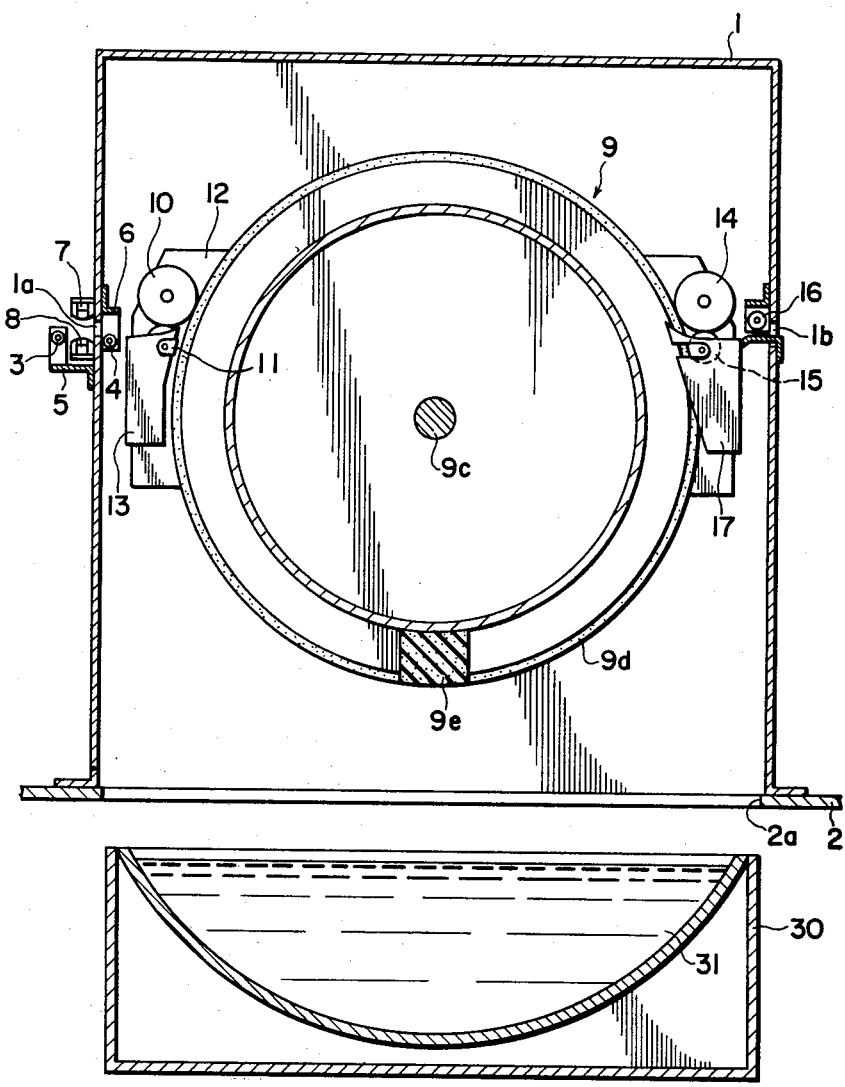
FIG. 1 and FIG. 2 show sectional side elevational views illustrating the construction of the conventional coloring-decoloring apparatus for an electrophoretic system.
Figure 2:
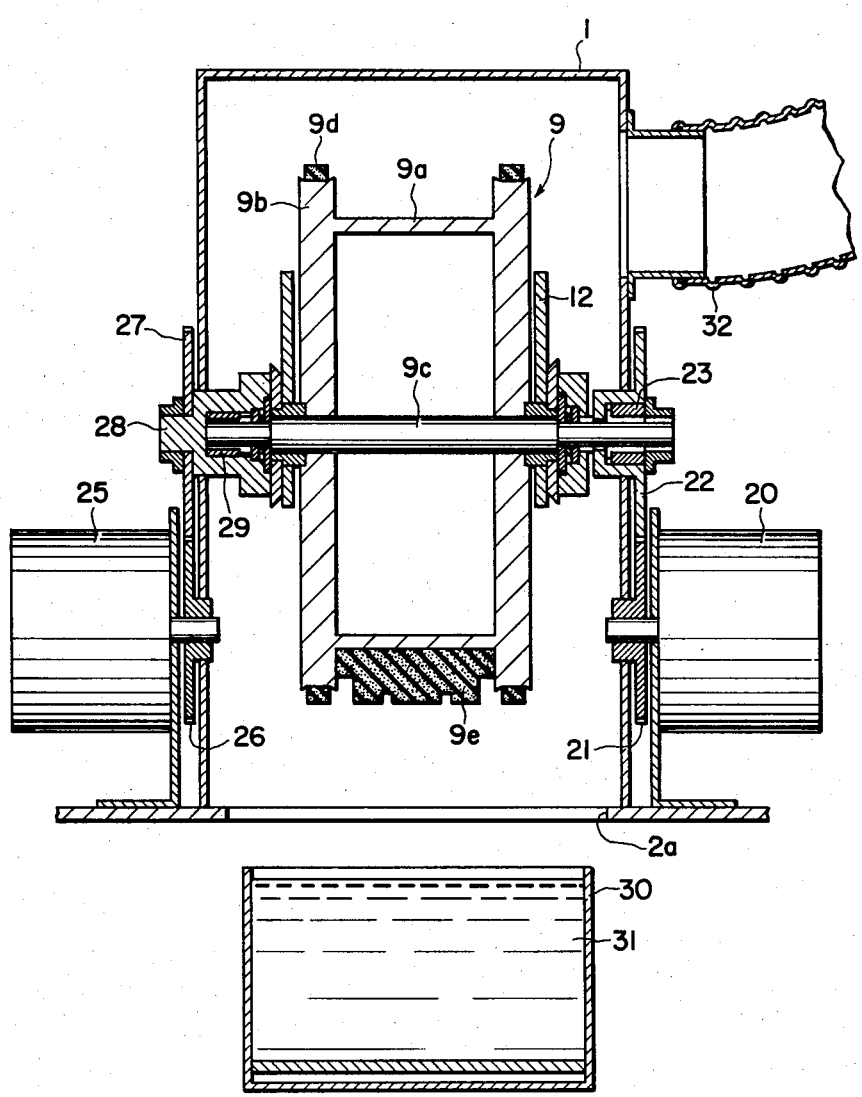

A driving system compatible with the embodiment is not limited to the one described above, and it will be possible to arrange driving systems separately on the right and left sides of the coloring-decoloring apparatus as shown in FIG. 1 and FIG. 2 illustrating the conventional example.

Figure 5:
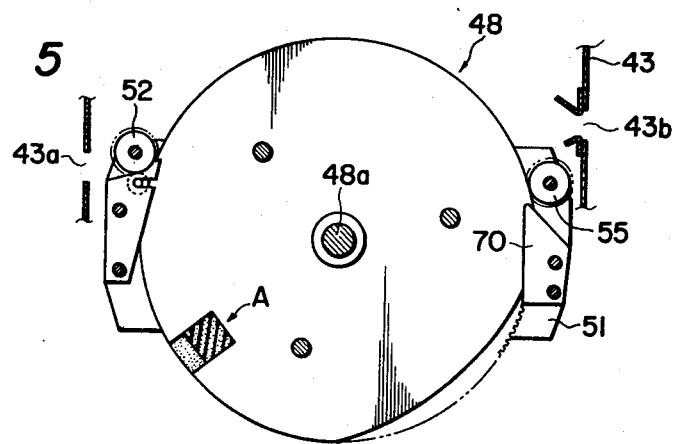
FIG. 5 through FIG. 7 show diagrams illustrating positional changes of the support plate and bonding drum in the coloring-decoloring apparatus according to the present invention.

Now, the function of the coloring-decoloring apparatus according to the present invention will be described in due sequence below. As soon as a sample carrier applied with a blood serum has been electrically energized in an electrophoretic apparatus as a process preceding the coloring and decoloring processes, the motor 71 of the driving system is driven so as to rotate its shaft 71a clockwise as seen from the right side of the drawing. This rotation causes the bonding drum 48 and the support plate to rotate as a unit until the pin on the pin holder plate 67 actuates the microswitch 65 for stopping them at the positions shown in FIG. 3. Subsequently, when the motor 71 is rotated in the reverse direction, the bonding drum 48 alone rotates and when the portion indicated by the reference symbol "A" of the drum (corresponding to the member 9e for adhering the sample carrier on the bonding drum 9 of the conventional apparatus) reaches point $B_1$, the pin on the pin holder plate 66 actuates microswitch 64 to stop the drum at the position shown in FIG. 5. On the other hand, a coloring liquid agent is supplied through the coloring liquid injection pipe 57 into the liquid trough 42 upon termination of the electrical energization of the sample carrier in the electrophoretic apparatus. Since the valve 61 is kept in its closed condition at this time, the liquid trough 42 is filled with the coloring liquid agent.

Figure 6:
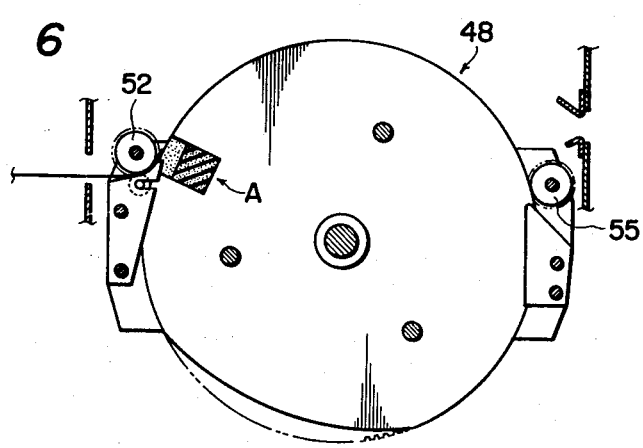
Figure 7:
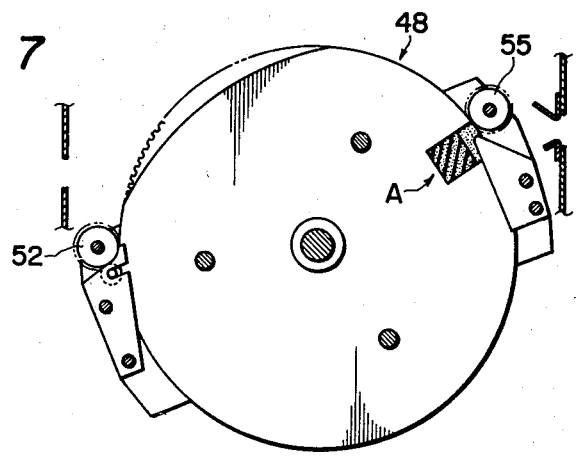

When the sample carrier is fed out of the electrophoretic apparatus subsequently, the shutter 47 opens and the sample carrier passes through the entrance opening. The photo sensor detects the passage of the sample carrier and the bonding drum 48 starts rotating. The sample carrier is inserted between the first and second rollers, and when the tip of the sample carrier reaches the surface of the bonding drum 48, the portion A of the drum which is preliminarily set at the point $B_1$ is placed in the vicinity of the first roller. Then, the sample carrier is fed while being bonded onto the bonding drum as illustrated in FIG. 6. Since the sample carrier is fed at the same speed as the rotating speed of the bonding drum in this condition, the sample carrier is not bonded onto the drum at the section 49a lower than the imaginary circular circumference of the drum but is kept a little loosened. When the bonding drum 48 is set at the position shown in FIG. 3, i.e., when the portion A reaches the third roller, the pin on the pin holder plate 66 actuates the microswitch 64 to stop the drum. Subsequently, when the motor 71 is driven so as to rotate the shaft 71a clockwise as seen from the right side of the drawing, the bonding drum 48 and support 51 rotate as a unit at a higher speed, thereby passing the sample carrier bonded onto the drum 48 several times through the coloring liquid agent filled in the liquid trough and being colored in this while. After this coloring process terminates, the valve 61 is opened to discharge the coloring liquid agent. Then, a decoloring liquid agent is injected like a shower from the decoloring liquid pipe 58 to splash and decolor the sample carrier which is being rotated as it is bonded onto drum 48. After this decoloring process terminates, the injection of the decoloring liquid agent is stopped and warm air is blown instead for drying the sample carrier. As the sample carrier is dried, it is gradually contracted and less loosened than the loose condition before drying along the surface 49a which is lower than the imaginary circular circumference of the bonding drum. Now, the coloring-decoloring apparatus completes all its operations and the rotation of the bonding drum 48 and support plate 51 as a unit stops with the portion A of the drum 48 or the third roller 55 set in the vicinity of the exit opening 43b, i.e., in the position shown in FIG. 7. Then, the shutter 56 is opened and the bonding drum 48 rotates to peel off the sample carrier from the bonding drum 48 by the guide plate 70 and feed it to the next stage through the exit opening 43b. When the next sample carrier is to be colored and decolored successively, the bonding drum 48 and support plate rotate as a unit until the support plate returns to the position shown in FIG. 3, and the bonding drum 48 alone further rotates until it is set at the start position. Then, the next sample carrier is colored, decolored and dried through the processes already described above.

As is understood from the foregoing descriptions, the coloring-decoloring apparatus according to the present invention has a superficial section which is lower than the imaginary circular circumference of the bonding drum which serves for maintaining a sample carrier in a loose condition while it is soaked, but in less loose condition after it is dried along the superficial section which is lower than the imaginary circular circumference of the bonding drum, thereby eliminating the fear of deformation or tearing of the sample carrier due to excessive tension. Further, the coloring-decoloring apparatus according to the present invention utilizes a lower section of the drum in the casing as a liquid trough and colors and decolors a sample carrier with coloring and decoloring liquid agents injected through coloring and decoloring liquid injection ports arranged in the liquid trough, thereby eliminating the necessity to provide large coloring and decoloring liquid troughs in the lower section of the casing and making it possible to design a compact coloring-decoloring apparatus. Furthermore, the coloring-decoloring apparatus according to the present invention eliminates the necessity to replace a coloring liquid trough with a decoloring liquid trough, thereby simplifying operations of the apparatus and making it possible to carry out coloring and decoloring of a sample carrier in a short time. Moreover, the coloring-decoloring apparatus according to the present invention is advantageous in that it requires no transporting mechanism for replacing liquid troughs with each other.

We claim:

1. A coloring-decoloring apparatus for electrophoretic systems, comprising: a mostly cylindrical bonding drum; means rotatably supporting said bonding drum;

said bonding drum having an arcuately extending outer peripheral region which is lower in curvature than the imaginary circular circumference of the remainder of the outer periphery of said drum;

a support plate which is arranged close to the outer periphery of said bonding drum;

two rollers mounted on said support plate and arranged to contact with said remainder of the outer periphery of said bonding drum and at a definite interval reserved therebetween which is greater than said lower in curvature region of said drum; a liquid trough which is so arranged as to dip a portion of said bonding drum with liquid;

means for filling said liquid trough with coloring liquid agent;

means for filling the same said liquid trough with decoloring agent;

said coloring-decoloring apparatus including means for bonding a sample carrier onto the outer periphery of said bonding drum while rotating said drum so as to overlay said peripheral region which is lower in curvature;

means for holding said sample carrier with said two rollers;

means for rotating said bonding drum and support plate as a unit to color said sample carrier when a coloring liquid agent is filled in said liquid trough and then to decolor said sample carrier by replacing said coloring liquid agent with a decoloring liquid agent in said liquid trough.

2. A coloring-decoloring apparatus for electrophoretic systems according to claim 1 wherein a coloring liquid injection port and a decoloring liquid injection port are arranged in said liquid trough.

3. A coloring-decoloring apparatus for electrophoretic systems according to claim 1 wherein a cover is mounted on said liquid trough for covering said bonding drum and said support plate.

4. A coloring-decoloring apparatus for electrophoretic systems according to claim 3 wherein a drying system is arranged for blowing air into the casing consisting of said liquid trough and said cover.

* * * * *